United States Patent [19]

Sugarman

[11] 3,971,644

[45] July 27, 1976

[54] MIXING AND DETOXIFICATION TANK WITH FILTRATION SYSTEM

[75] Inventor: Edward D. Sugarman, Fayetteville, N.Y.

[73] Assignee: Wal-Gen Corporation, Syracuse, N.Y.

[22] Filed: Aug. 28, 1974

[21] Appl. No.: 501,025

[52] U.S. Cl. .................................... 55/387; 312/1
[51] Int. Cl.² ........................................ B01D 53/34
[58] Field of Search .......... 23/232 E, 232 C, 232 R; 210/501, 94, 41; 55/387, 385; 34/72, 82; 128/1 R, 1 B, 191 A, 277, 298, 299; 312/1

[56] References Cited
UNITED STATES PATENTS

| | | | |
|---|---|---|---|
| 2,039,490 | 5/1936 | Mikelson | 312/1 |
| 2,729,337 | 1/1956 | Alferman | 210/169 X |
| 2,786,740 | 3/1957 | Tayor et al. | 128/1 B |
| 3,335,713 | 8/1967 | Grosholz et al. | 128/1 B |
| 3,785,377 | 1/1974 | Jorgensen | 128/188 |
| 3,788,047 | 1/1974 | Douthitt | 55/387 |

Primary Examiner—Charles N. Hart
Assistant Examiner—Robert H. Spitzer
Attorney, Agent, or Firm—Bruns & Jenney

[57] ABSTRACT

A mixing tank and filtration system for operating room use. The tank is utilized for mixing a cement that is employed in reconstructing joints such as the hip joint, and mixing must take place in the operating room because the cement sets up in a very short time. The only presently approved cement gives off toxic fumes during the mixing which fumes frequently have a detrimental effect on the patient and operating room personnel. The mixing tank and filtration system disclosed herein are constructed and arranged to contain and draw off the toxic fumes whereby the detrimental effects on personnel are eliminated.

2 Claims, 1 Drawing Figure

U.S. Patent   July 27, 1976   3,971,644
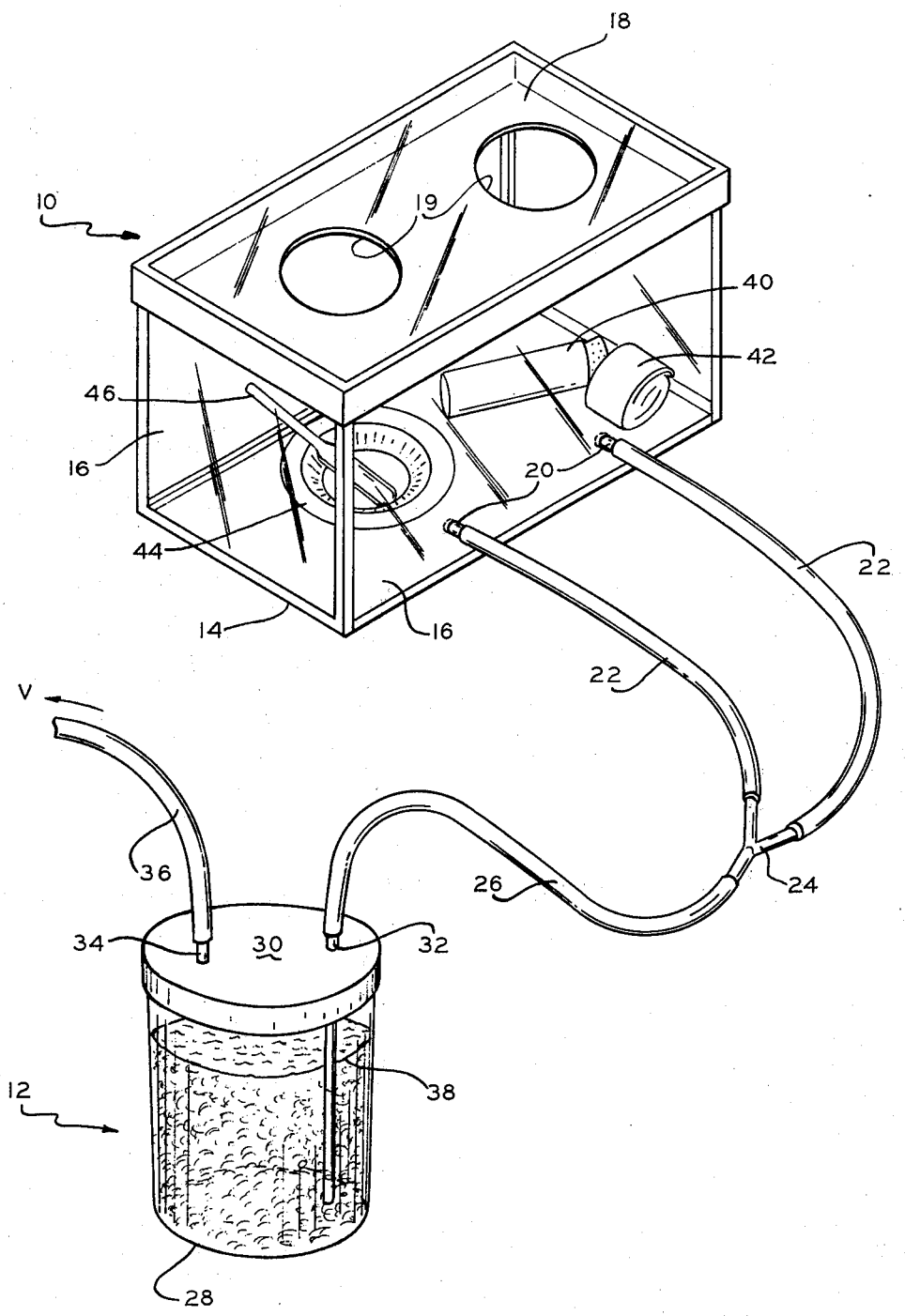

MIXING AND DETOXIFICATION TANK WITH FILTRATION SYSTEM

BACKGROUND OF THE INVENTION

This invention relates generally to apparatus for carrying out a mixing operation in a controlled environment. More particularly, the invention is directed to a novel mixing tank and filtration system that prevent toxic fumes, given off during a mixing operation, from permeating the surrounding atmosphere.

While not restricted to such use, the mixing and detoxification apparatus of the invention is particularly well adapted for use in a hospital operating room when it is necessary to mix a special cement used in a certain type of orthopaedic surgery. Thus, in reconstructing joints such as a hip, knee or finger joint, a methylmethacrylate cement is used. This cement must be mixed in the operating room while the operation is in process because it sets up in a matter of minutes.

Heretofore, the cement has been mixed in the open and during the mixing monomer fumes are given off which are toxic. These fumes frequently cause nausea and headaches to operating room personnel and may have other detrimental effects. Insofar as the applicant is aware, no apparatus or process has been available to alleviate this situation prior to the present invention.

SUMMARY OF THE INVENTION

The invention disclosed herein is essentially comprised of a mixing tank and a filtration system. The tank is provided with a removable cover so that the cement ingredients can be placed in the tank and the mixed cement removed therefrom. The tank cover has two arm holes to enable one to put his hands in the tank to do the mixing. The arm holes are large enough so that ambient air can be drawn through them around the arms of the person doing the mixing.

The toxic fumes that are given off during the mixing are heavier than air and tend to settle at the bottom of the tank where the latter is provided with one or more exhaust ports. The exhaust ports are connected by suitable conduits to the inlet port of a filter receptacle, the outlet port of which is connected to the operating room vacuum system. The filter receptacle contains activated carbon and water and the fumes from the mixing tank bubble up through this mixture with the result that they are rendered substantially non-toxic.

The mixing tank is at least in part made of transparent material to enable the person doing the mixing to see what he is doing. Both the mixing tank and the filtration receptacle can be fully gas sterilized.

BRIEF DESCRIPTION OF THE DRAWING

The single drawing FIGURE is a top perspective view of a mixing tank and filtration system embodying the invention.

DESCRIPTION OF THE PREFERRED EMBODIMENT

Having reference now to the drawing, the mixing tank is generally indicated at 10 and the filtration system at 12. The tank is comprised of a bottom 14, side walls 16 and a removable top 18. The tank can be any convenient shape and needs only to be large enough to permit the cement to be manually mixed.

To enable the person doing the mixing to see what he is doing, at least the top, and preferably the top and sides, of the tank are made of transparent material such as glass or clear plastic. The top is formed with a pair of arm holes 19 to enable a person to put his hands in the tank to do the mixing as will presently be described in more detail.

Just above its bottom 14, the tank is provided with a pair of exhaust ports in the form of short tubes 20 which pass through one of the side walls 16. These tubes are connected by flexible conduits 22 to two of the branches of a Y connector 24, the leg of the connector being connected to the filtration system 12 by means of a flexible conduit 26. The principal part of the filtration system is a jar-like receptacle 28 having a removable top closure or cover 30.

The cover 30 is provided with inlet and outlet ports in the form of tubes 32,34 which pass through the cover as indicated in the drawing. The outer end of inlet tube 32 is connected to conduit 26 and the inner end of the tube terminates just above the bottom of receptacle 28. The outer end of outlet tube 34 is connected by a flexible conduit 36 to the operating room vacuum system (not shown) or other suitable vacuum source. The inner end of the outlet tube terminates above the level of the liquid 38 that is in the receptacle 28, the liquid being water with activated carbon suspended therein.

As previously stated, the apparatus of the invention can be used advantageously for any mixing operation in which toxic fumes are given off. In describing its use, however, reference will be made to the mixing of methylmethacrylate cement for use in orthopaedic surgery as in reconstructing a hip joint. Methylmethacrylate must be used for this purpose as it is the only material presently approved by the Food and Drug Administration. At the same time, the material is classified as a toxic substance under the Occupational Safety and Health Act and, as noted above, the toxic fumes given off during mixing frequently cause nausea and headaches to operating room personnel.

The methylmethacrylate cement is mixed in the operating room while the operation is in process because it starts setting up in about 4 minutes and is rock hard in 10–12 minutes. Accordingly, the mixing tank 10 and filtration system 12 are placed on a table in the operating room and the conduit 36 is connected to the operating room vacuum system. The ingredients of the cement are methylmethacrylate in liquid and powder forms. The liquid methylmethacrylate is highly volatile and is contained in a glass vial 40. The powdered methylmethacrylate is usually contained in a packet 42, the vial and packet being placed in tank 10 prior to the operation.

When it is time to mix the cement, the surgeon or an assistant puts his arms through the arm holes 19, opens the vial and packet and empties their contents into a shallow disposable dish 44. The ingredients are then mixed together with a suitable instrument such as a spatula 46. During the reaction that occurs, there is a vaporization of the liquid that is in excess of that required to mix with the powder and it is these vapors or fumes that are toxic.

The toxic monomer fumes are heavier than air and thus tend to settle at the bottom of tank 10 where they are drawn off through exhaust ports 20. The fumes pass through conduits 22,26 and enter the filter receptacle near the bottom thereof. This causes the fumes to bubble up through the water and activated carbon mixture 38 which renders the fumes substantially non-toxic. The harmless fumes that emerge at the top of the liquid are evacuated from the filter receptacle through conduit 36 by the operating room vacuum system.

As the toxic fumes are drawn from the mixing tank through the exhaust ports 20, ambient air enters the tank through the arm holes 19 which are large enough to permit entry around the arms of the person doing the mixing. This non-sealing relation between the arm holes and arms of the mixer is important because the ambient air operates to flush out the tank and insure that there will be a continuous outflow of the toxic fumes through the exhaust ports.

Upon completion of the operation, the vial 40, packet 42 and mixing dish 44 can be thrown away and the mixing tank and filtration system gas sterilized in preparation for their next use.

From the foregoing description, it will be apparent that the invention disclosed herein provides a novel and highly beneficial mixing and detoxificaion apparatus. As will be understood by those familiar with the art, the invention may be embodied in other specific forms without departing from the spirit or essential characteristics thereof.

I claim:

1. For use with a hospital vacuum source, operating room mixing and detoxification apparatus comprising a tank having a bottom, side walls and a removable top, at least the side walls and top of the tank being made of transparent material, the tank being particularly adapted for mixing a cement that gives off toxic fumes during the mixing, the top of the tank being formed with a pair of open arm holes through which the arms of an operator can extend downwardly into the tank interior to do the mixing, the holes being dimensioned so as to encircle the operator's arms with a close but non-sealing fit whereby ambient room air can pass through the holes around the operator's arms and assist in flushing toxic fumes out of the tank, and filtration means for the tank, the tank having at least one exhaust port located adjacent the bottom thereof, the exhaust port being connected through the filtration means to the hospital vacuum source.

2. Apparatus as defined in claim 1 wherein said closed receptacle contains activated carbon and water, said inlet and outlet ports being arranged so that gases drawn into the receptacle from said tank pass through the carbon and water before leaving the receptacle.

* * * * *